United States Patent
Okamoto et al.

(10) Patent No.: US 6,641,784 B1
(45) Date of Patent: Nov. 4, 2003

(54) OPTICALLY ACTIVE ISOCYANURATE AND OPTICAL RESOLVER COMPRISING DERIVATIVE OF THE SAME

(75) Inventors: Yoshio Okamoto, Aichi (JP); Motohiko Hidaka, Chiba (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 10/048,992

(22) PCT Filed: Aug. 18, 2000

(86) PCT No.: PCT/JP00/05568

§ 371 (c)(1),
(2), (4) Date: Feb. 19, 2002

(87) PCT Pub. No.: WO01/14288

PCT Pub. Date: Mar. 1, 2001

(30) Foreign Application Priority Data

Aug. 19, 1999 (JP) ............................................. 11232216

(51) Int. Cl.[7] ............................................... G01N 30/48
(52) U.S. Cl. .......................... 422/70; 210/635; 436/161; 544/192; 549/541; 549/542; 528/418
(58) Field of Search ........................ 528/418; 544/192; 549/541, 542; 210/635; 422/70; 436/161

(56) References Cited

U.S. PATENT DOCUMENTS 5,892,065 A    4/1999    Tsukamoto et al.
6,111,104 A    8/2000    Ikeda et al.
6,124,454 A    9/2000    Ikeda et al.
6,177,541 B1   1/2001    Ikeda et al.
6,444,814 B1 * 9/2002    Ikeda et al. ................. 544/192

FOREIGN PATENT DOCUMENTS

JP    2-279684    11/1990
WO    99/45005    9/1999

* cited by examiner

Primary Examiner—Robert Dawson
Assistant Examiner—D. Aylward
(74) Attorney, Agent, or Firm—Oblon, Spivak, McClelland, Maier & Neustadt, P.C.

(57) ABSTRACT

An optical resolver comprising an optically active substance made of tris-(2,3-epoxypropyl)isocyanurate, is presented. The optical resolver comprises an optically active tris-(epoxyalkyl)isocyanurate or its derivative, or an optically active derivative of a tris-(epoxyalkyl)isocyanurate. Particularly, the optical resolver comprises optically active tris-(2,3-epoxypropyl)isocyanurate or its derivative, or an optically active derivative of tris-(2,3-epoxypropyl) isocyanurate. Having supported on a carrier, an optically active tris-(2,3-epoxypropyl)isocyanurate or its derivative, or an optically active derivative of tris-(2,3-epoxypropyl) isocyanurate, can be made to be a packing for use in high-performance liquid chromatography, whereby efficient optical resolution can be carried out.

20 Claims, No Drawings

OPTICALLY ACTIVE ISOCYANURATE AND OPTICAL RESOLVER COMPRISING DERIVATIVE OF THE SAME

TECHNICAL FIELD

The present invention relates to an optically active gent comprising optically active tris-(2,3-epoxypropyl) isocyanurate or an optically active derivative of tris-(2,3-epoxypropyl)isocyanurate, which may be supported on surface-modified carrier to form an optical resolver suitable for high-performance liquid chromatography.

BACKGROUND ART

In recent years, development of functional polymers intended for recognizing molecules, has been remarkable, and functional polymers capable of recognizing objective ions, organic low molecules and polymer compounds by their sizes, shapes, electric charges, etc., have been researched and developed. On the other hand, in the field of pharmaceuticals, many cases have been known in which pharmacological effects are different among optical isomers. For example, with respect to thalidomide, it is known that only (S)-(−) isomer has teratogenicity. Like this, with pharmaceuticals, it is not rare that only one of optical isomers of the compound to be used, brings about a strong side effect.

For such a reason, also in the field of recognizing molecules, an attention has been drawn particularly to a functional polymer having an asymmetry-recognizing ability. With respect to such a functional polymer having an asymmetry-recognizing ability, some technologies are known, and possible applications to a packing for an optical resolution chromatography column, a membrane for optical resolution or a host for a host-guest method, have been researched, studied and developed. Among them, an application to a packing for an optical resolution chromatography column has been active. The optical resolution chromatography is known to be very effective as a means for an optical resolution, since an optically active substance can be easily and simply analyzed and separated. Asymmetry-recognizing polymers so far researched and developed as packings for optical resolution chromatography columns include, polysaccharides such as cellulose triacetate (JP-A-59-166502, etc.), cellulose benzoate (JP-A-60-40952, etc.), cellulose carbamate (JP-A-60-108751, etc.) and amylose carbamate (JP-A-60-226831, etc.), synthetic polymers, for example, proteins such as bovine serum albumin (J. Chromatogr., 264(1983), 63–68, etc.), α1-acid glycoprotein (J. Chromatogr., 269(1983), 71–80, etc.) and ovomucoid (JP-A-4-187646, etc.), a poly(meth)acrylic acid amide (JP-A-51-81891, etc.), and a poly(meth)acrylic acid ester (JP-A-56-142216, etc.).

On the other hand, Inoue et al. have reported on molecular design and utilization of novel optically active isocyanurates at 1998 Annual Meeting of Chemical Society of Japan (Report No. 1G414, 1G415) and at 1999 Annual Meeting of Chemical Society of Japan (Report No. 1D244, 1D245). In these reports, a discussion is made with respect to asymmetry-recognition, but no discussion is made on optical resolution.

These asymmetry-recognizing polymers have strong and weak points for optical resolution depending upon the objective compounds, whereby the respective ranges of the objective compounds for optical resolution have been limited.

It is an object of the present invention to provide a novel optical resolver employing an optically active tris-(2,3-epoxypropyl)isocyanurate or its derivative, or an optically active derivative of tris-(2,3-epoxypropyl)isocyanurate, in order to broaden the range of objective compounds for optical resolution.

The present inventors have conducted an extensive study to invent a novel optically active compound as a novel optical resolver, whereby they have found that an optically active compound employing tris-(2,3-epoxypropyl) isocyanurate as the starting material, is useful as an optical resolver and have accomplished the present invention.

DISCLOSURE OF THE INVENTION

The first aspect of the present invention is an optical resolver comprising an optically active tris-(epoxyalkyl) isocyanurate or its derivative.

The second aspect is the optical resolver according to the first aspect, wherein the optically active tris-(epoxyalkyl) isocyanurate is optically active tris-(2,3-epoxypropyl) isocyanurate.

The third aspect is an optical resolver comprising an optically active derivative of a tris-(epoxyalkyl) isocyanurate.

The fourth aspect is the optical resolver according to the third aspect, wherein the optically active derivative of a tris-(epoxyalkyl)isocyanurate is an optically active derivative of tris-(2,3-epoxypropyl)isocyanurate.

The fifth aspect is the optical resolver according to the fourth aspect, wherein the optically active derivative of tris-(2,3-epoxypropyl)isocyanurate is one obtained by a reaction of tris-(2,3-epoxypropyl)isocyanurate with an optically active compound.

The sixth aspect is an optical resolver having an optically active tris-(epoxyalkyl)isocyanurate or its derivative, or an optically active derivative of a tris-(epoxyalkyl) isocyanurate, supported on a carrier.

The seventh aspect is an optical resolver having optically active tris-(2,3-epoxypropyl)isocyanurate or its derivative, or an optically active derivative of tris-(2,3-epoxypropyl) isocyanurate, supported on a carrier.

BEST MODE FOR CARRYING OUT THE INVENTION

The optical resolver in the present invention is an optically active compound employing, as a starting material, an epoxy compound having an isocyanurate ring. Namely, it is required to have an isocyanurate ring, an asymmetric center based on an epoxy group and an optical activity. For example, when optically active tris-(2,3-epoxypropyl) isocyanurate is used, it has a tris-(propyl)isocyanurate structure having an optically active asymmetric center at the 2-position. When racemic tris-(2,3-epoxypropyl) isocyanurate is used, it has a tris-(propyl)isocyanurate structure having an asymmetric center at the 2-position and an optically active point derived from an optically active compound which is present in the vicinity thereof. Namely, the present invention can not be accomplished when a tris-(propyl)isocyanurate structure having no asymmetric center is used in a case where no epoxy compound is used as the starting material, or when a racemic tris-(2,3-epoxypropyl) isocyanurate is used alone.

In a first embodiment, the present invention provides an optical resolver comprising an optically active tris-(epoxyalkyl)isocyanurate or its derivative. The optically active tris-(epoxyalkyl)isocyanurate may be one wherein the alkyl part is an alkyl group having from 2 to 6 carbon atoms, and it may, for example, be optically active tris-(2,3-epoxypropyl)isocyanurate or optically active tris-(2,3-epoxy-2-methylpropyl)isocyanurate. However, optically active tris-(2,3-epoxypropyl)isocyanurate is preferably employed.

The optically active tris-(epoxyalkyl)isocyanurate itself, preferably the optically active tris-(2,3-epoxypropyl)isocyanurate itself, may be used as it is. However, when it is to be used as a packing for high performance liquid chromatography, it is preferably used as fixed on a carrier by physical adsorption or chemical reaction. In a case where it is to be chemically fixed, the carrier surface is modified with a compound having a reactive functional group (A), and by permitting the reactive functional group (A) and the epoxy group of an optically active tris-(2,3-epoxypropyl)isocyanurate to react, an optical resolver having the optically active tris-(2,3-epoxypropyl)isocyanurate derivative supported thereon, can be obtained. Here, it is preferred to react at least one functional group of the reactive functional group (A) to one molecule of the optically active tris-(2,3-epoxypropyl)isocyanurate. This is intended to prevent flowing out of the tris-(2,3-epoxypropyl)isocyanurate from the column by dissolution under an influence of an eluent used or by being detached by a physical force when the tris-(2,3-epoxypropyl)isocyanurate itself is used as a packing for e.g. high performance liquid chromatography to carry out optical resolution by using it as an optical resolver, whereby deterioration of the separation ability can be prevented, and a preferred packing useful for a long period of time can be obtained.

Further, in a case where unreacted epoxy groups remain in the optical resolver, they are likely to react with e.g. an alcohol which is used at the time of optical resolution, whereby the asymmetry-recognizing ability may change with time. Accordingly, it is preferred to preliminarily react the remaining epoxy groups with a compound having a reactive functional group (A) or with an optically active compound, before use.

In the present invention, it is preferred to use an optical resolver wherein the tris-(2,3-epoxypropyl)isocyanurate of the first embodiment itself is an optically active substance, whereby the range of compounds which can be subjected to optical resolution is broadened.

In a second embodiment, the present invention provides an optical resolver comprising an optically active derivative of a tris-(epoxyalkyl)isocyanurate. The optically active derivative of a tris-(epoxyalkyl)isocyanurate may be one wherein the alkyl part is an alkyl group having from 2 to 6 carbon atoms, such as an optically active derivative of tris-(2,3-epoxypropyl)isocyanurate or an optically active derivative of tris-(2,3-epoxy-2-methylpropyl)isocyanurate. It is particularly preferred to employ an optically active derivative of tris-(2,3-epoxypropyl)isocyanurate. The optically active derivative of tris-(2,3-epoxypropyl)isocyanurate can be obtained by a method of reacting at least one molecule of an optically active compound (B) having at least one asymmetric carbon and a reactive functional group (A) in one molecule, to one molecule of tris-(2,3-epoxypropyl)isocyanurate.

The optically active derivative of a tris-(epoxyalkyl)isocyanurate, preferably the optically active derivative of tris-(2,3-epoxypropyl)isocyanurate, is employed preferably as fixed on a carrier by physical adsorption or chemical reaction, rather than being used by itself.

In a case where it is to be chemically fixed, the carrier surface may be modified, for example, with a compound having a reactive functional group (A), and the reactive functional group (A) is reacted with an epoxy group of the tris-(2,3-epoxypropyl)isocyanurate, and further an optically active compound (B) having at least one asymmetric carbon and a reactive functional group (A) in one molecule, may be further reacted, whereby an optical resolver having the optically active derivative of tris-(2,3-epoxypropyl)isocyanurate supported on the carrier, can be obtained. By selecting the reactive functional group (A) in the optically active compound (B) or the main framework, it is possible to obtain an optical resolver which is applicable widely to various compounds.

The method for producing the tris-(epoxyalkyl)isocyanurate to be used in the present invention, is not particularly limited. For example, tris-(2,3-epoxypropyl)isocyanurate can be prepared by reacting epichlorohydrin to cyanuric acid, followed by dropwise addition of an aqueous NaOH solution while carrying out dehydration refluxing, whereby a dehydrochloric acid reaction takes place, whereby tris-(2,3-epoxypropyl)isocyanurate as the desired product, is obtainable. The optically active tris-(2,3-epoxypropyl)isocyanurate can be produced by using an optically active substance of the above epichlorohydrin.

The tris-(2,3-epoxypropyl)isocyanurate has three asymmetric carbon atoms in one molecule. (2R,2'R,2"R)-tris-(2,3-epoxypropyl)isocyanurate and (2S,2'S,2"S)-tris-(2,3-epoxypropyl)isocyanurate, wherein all such three asymmetric carbon atoms are consistent, are optically active tris-(2,3-epoxypropyl)isocyanurates, and they are useful in the first embodiment of the present invention.

On the other hand, a raceme (β-form crystals) which is an equimolar mixture of the above-mentioned R-isomer and S-isomer, or a mixture (α-form crystals) of (2R,2R,2S)-tris-(2,3-epoxypropyl)isocyanurate and (2S,2S,2R)-tris-(2,3-epoxypropyl)isocyanurate wherein only one among the three asymmetric carbon atoms is different in steric configuration, or a mixture of such α-form crystals and β-form crystals, is useful in the second embodiment of the present invention.

The tris-(2,3-epoxypropyl)isocyanurate and its optically active substance to be used in the present invention, are preferably of high purity from the nature of their application. Specifically, a purity of at least 90% is preferred. More preferably, the purity is at least 95%. In the case of optically active tris-(2,3-epoxypropyl)isocyanurate, the optical purity is also important. Preferably, the optical purity is at least 80%e.e., and more preferably, the optical purity is at least 90%e.e.

The method for purification is not particularly limited. For example, purification can be carried out by recrystallizing the obtained tris-(2,3-epoxypropyl)isocyanurate or its optically active substance from a solvent such as methanol. Further, a highly purified product of tris-(2,3-epoxypropyl)isocyanurate is marketed under a tradename of TEPIC-S by Nissan Chemical Industries, Ltd. and readily available.

In the present invention, the compound having a reactive functional group (A) is a compound which is capable of reacting with an epoxy group or an epoxy derivative, and it is preferably a compound having a functional group having at least one active hydrogen. For example, a usual active hydrogen group such as a carboxyl group (—COOH), an amino group (—NH$_2$), an imino group (=NH), a hydroxyl group (—OH) or a thiol group (—SH), may be mentioned. As a special group, an isocyanate group (—NCO) is also reactive with an epoxy group or an epoxy derivative, and may therefore be included in such a category. In a case where a compound having an isocyanate group (—NCO) as the reactive functional group (A), is used, it may be reacted directly with an epoxy group to form an oxazolidinon ring which is an urethane of 5-membered ring. However, it may be reacted with a hydroxyl group (—OH) as a ring-opened product derived from an epoxy group formed by reacting the epoxy group with other active hydrogen group, or it may further be reacted with an amino group (—NH$_2$) or a thiol group (—SH) formed by the reaction with ammonia or hydrogen sulfide.

Such a compound may be represented as a monofunctional compound by a carboxyl group-containing compound (R—COOH), an amino group-containing compound (R—NH$_2$), an imino group-containing compound (R'(=NH)), an isocyanate group-containing compound (R—NCO), a hydroxyl group-containing compound (R—OH) or a thiol group-containing compound (R—SH), and as a polyactive hydrogen compound, by a polycarboxyl group-containing compound (R$^1$(COOH)$_n$), a polyamino group-containing compound (R$^1$(—NH$_2$)$_n$), a polyimino group-containing compound (R$^{1'}$(=NH)$_n$), a polyisocyanate group-containing compound (R$^1$(—NCO)$_n$), a polyhydroxyl group-containing compound (R$^1$(—OH)$_n$) or a olythiol group-containing compound (R'(—SH)$_n$). R, R', R$^1$ and R$^{1'}$ are not particularly limited, but R represents a monovalent substituent such as hydrogen, or a C$_1$–C$_{20}$ aliphatic hydrocarbon or a C$_6$–C$_{20}$ aromatic hydrocarbon, R$^1$ is a n-valent substituent, preferably a C$_1$–C$_{20}$ aliphatic hydrocarbon or a C$_6$–C$_{20}$ aromatic hydrocarbon. R' in the case of an imino group-containing compound, represents a bivalent substituent, and R$^{1'}$ represents a 2×n valent substituent. More specifically, R is preferably, for example, a strait chain alkyl group such as a methyl group, an ethyl group, a butyl group or an octadecyl group, or a cycloalkyl group such as a cyclopentyl group or a cyclohexyl group, as classified into an alkyl group, or an aromatic hydrocarbon group such as a phenyl group, a naphthyl group, a biphenyl group or an anthryl group, which may be substituted by heteroatoms or may have branches. In the polyactive hydrogen compound, n has a natural number, and R$^1$ represents a bivalent substituent corresponding to R. For example, as a hydroxyl group-containing compound (R$^1$(—OH)$_n$) which is a compound based on a phenyl group and wherein n=3, trimesic acid or trimellitic acid may be mentioned. R' and R$^{1'}$ may also be represented like R and R$^{1'}$, and groups corresponsing to the substituents exemplified for R may be mentioned as preferred. For example, as one corresponding to an alkyl group, a straight chain alkylidene group such as a methylene group, an ethylidene group, a butylidene group, an octadecylidene group or a cycloalkylidene group such as a cyclopentylidene group or a cyclohexylidene group, corresponding to an alkylidene group, may be mentioned. An imino group-containing compound is special, and as a specific compound, aziridine, azetidine, pyrrolidine, pyrroline or pyrrol may be exemplified, and further, as a polyimino group-containing compound, imidazolidine, pyrazolidine, piperazine or triethylene tetramine, may, for example, be mentioned.

The optically active compound (B) having at least one asymmetric carbon atom and a reactive functional group (A) in one molecule, to be used in the present invention, falls in the category of the above-mentioned compound having a reactive functional group (A). As such an optically active compound (B), the purity is preferably at least 90%, and more preferably the purity is at least 95%. The optical purity is preferably at least 80%e.e., and more preferably, the optical purity is at least 90%e.e. As such an optically active compound (B), an amino acid or the like may also be mentioned, but a compound having an aromatic group in the vicinity of asymmetric carbon is preferred. For example, as an amino group-containing compound, an alkylbenzyl amine such as methylbenzyl amine, may be mentioned, and as an isocyanate group-containing compound, an alkylbenzyl isocyanate such as methylbenzyl isocyanate may, for example, be mentioned.

Further, as the most preferred optically active compound (B) in the present invention, an alkylbenzyl isocyanate such as methylbenzyl isocyanate, may be mentioned.

In the present invention, the optically active tris-(2,3-epoxypropyl)isocyanurate or the optically active derivative of tris-(2,3-epoxypropyl)isocyanurate, can be applied to an optical resolution method which is commonly known, for example, as a host for a host-guest method or a preferential crystallization method. However, it may be pulverized to a particle size within a proper range, or may be granulated by e.g. agglomeration, and then packed into a stainless steel column for high performance liquid chromatography (HPLC), so that it is useful as an optical resolver. More preferably, it may be supported on a carrier by surface modification, whereby it can be used more effectively as an optical resolver.

As a carrier, a porous carrier is preferred. For example, a porous inorganic carrier of e.g. silica, alumina, magnesia, titanium oxide, glass, a silicate or kaoline or a porous organic carrier of e.g. polystyrene, polyamide or polyacrylate, may be mentioned. However, an inorganic porous particles of e.g. silica (silica gel) or glass (porous glass), are preferred. Particularly preferred is silica gel.

A preferred particle size of such a porous carrier varies depending upon the particular application, but it is usually from 1 μm to 10 mm, preferably from 1 μm to 300 μm. With respect to pore physical properties, the average pore radius in a dried state as measured by a BET method, is from 10 Å to 10 μm, preferably from 20 Å to 2,000 Å, and the pore surface area is from 1 to 2,000 m$^2$/g, preferably from 5 to 1,500 m$^2$/g.

The modification method of the optically active, or the α-form, β-form or mixed form tris-(2,3-epoxypropyl) isocyanurate on such a porous carrier, may, for example, be an adsorption modification method wherein the optically active, or the α-form, β-form or mixed form tris-(2,3-epoxypropyl)isocyanurate is dissolved in a solvent and subjected together with a porous carrier to removal of the solvent by e.g. an evaporator, to have it adsorbed on the surface of the porous carrier, or a chemical modification method wherein it is chemically bonded on the porous carrier. Preferred is a chemical modification method, and by having it chemically bonded, it is possible to suppress detachment, by a physical force and by dissolution, of the modified optically active tris-(2,3-epoxypropyl) isocyanurate or its derivative, or the optically active derivative of tris-(2,3-epoxypropyl)isocyanurate by the developing solvent when optical resolution is carried out by HPLC, whereby the useful time has an optical resolver will be prolonged, such being industrially advantageous.

As a method for chemical modification of the carrier surface, any method may be employed since such a method is not substantially concerned with the action for optical resolution. For example, silanol groups on a carrier surface such as silica gel surface, may directly be reacted with non-reacted epoxy groups as tris-(2,3-epoxypropyl)

isocyanurate residues in an optically active derivative of tris-(2,3-epoxypropyl)isocyanurate, or with hydroxyl groups formed by the reaction with a compound containing active hydrogen.

Preferably, by using a surface treating agent having functional groups capable of reacting with both the carrier and the epoxy group of tris-(2,3-epoxypropyl)isocyanurate, firstly, the carrier surface is modified, and then, the surface treating agent on the carrier surface is reacted with the epoxy group in the optically active, or the α-form, β-form or mixed form tris-(2,3-epoxypropyl)isocyanurate, whereby surface modification can effectively be carried out.

In the case of silica gel, as an example, the surface treating agent may be a compound which contains both the above-mentioned reactive functional group (A) and a substituent capable of being reacted with silanol groups (≡Si—OH) remaining on the silica gel surface, such as a polyol, a polyisocyanate or a commonly employed coupling agent such as a titanate type or silane type coupling agent.

The titanate type coupling agent may, for example, be isopropyl tri(N-aminoethyl-aminoethyl) titanate, and the silane type coupling agent may, for example, be N-β (aminoethyl) γ-aminopropyl methyl dimethoxysilane, N-β (aminoethyl) γ-aminopropyl trimethoxysilane, N-β (aminoethyl) γ-aminopropyl triethoxysilane, γ-aminopropyl trimethoxysilane, γ-aminopropyl triethoxysilane, or γ-mercaptopropyl trimethoxysilane.

On the other hand, even a compound having no reactive functional group (A) may be used so long as a reactive functional group (A) can be introduced to the carrier surface by conversion into a functional group or by a reaction with a compound having at least two functional groups (A). For example, β-(3,4-epoxycyclohexyl) ethyltrimethoxysilane, γ-glycidoxypropyl trimethoxysilane, γ-glycidoxypropyl triethoxysilane or γ-glycidoxypropylmethyl diethoxysilane may be mentioned. A method will be specifically exemplified. Namely, the present invention can be carried out also by reacting an alkoxysilane (≡Si—O—R) of a surface treating agent to silanol groups (≡Si—OH) remaining on the silica gel surface to bond them by dealcoholization condensation, and then reacting a compound having an at least bi-functional reactive functional group (A) such as ammonia or hydrogen sulfide, to the epoxy group (the glycidoxy group) remaining in the surface treating agent.

A preferred surface treating agent to be used in the present invention is a titanate type or silane type coupling agent. Among them, a silane type is preferred and for example, an aminosilane type N-β (aminoethyl) γ-aminopropyl methyldimethoxysilane, N-β (aminoethyl) γ-aminopropyl trimethoxysilane, N-β (aminoethyl) γ-aminopropyl triethoxysilane, γ-aminopropyl trimethoxysilane or γ-aminopropyl triethoxysilane may be mentioned as preferred.

Here, as a preferred form of the optical resolver in the present invention, a method for its preparation will be specifically exemplified.

Now, a case (the first embodiment) wherein optically active tris-(2,3-epoxypropyl)isocyanurate is used, will be described. As the carrier, silica gel may be mentioned as an example.

In the first step, the silica gel surface is subjected to surface treatment with e.g. a silane type coupling agent having a reactive functional group (A) in its molecule, whereby the silica gel surface is chemically modified.

In the second step, the reactive functional group (A) in the silane coupling agent on the silica gel surface is reacted with the optically active tris-(2,3-epoxypropyl)isocyanurate to have the optically active tris-(2,3-epoxypropyl)isocyanurate derivative supported on the carrier surface. (0 Generation)

In the third step, a compound (such as ammonia) having a reactive functional group (A) is reacted to a non-reacted epoxy group of the optically active tris-(2,3-epoxypropyl) isocyanurate derivative supported on this carrier surface.

In the fourth step, optically active tris-(2,3-epoxypropyl) isocyanurate is further reacted to the carrier having the optically active tris-(2,3-epoxypropyl)isocyanurate derivative having active hydrogen (amino group) at its terminal, supported thereon, obtained in the third step, to form two layers of the optically active tris-(2,3-epoxypropyl) isocyanurate derivative, on the silica gel. (The first generation type)

The fifth step et seq. are steps wherein the third and fourth steps are repeated to laminate the optically active tris-(2,3-epoxypropyl)isocyanurate layers.

As the optical resolver of the present invention, any one of those obtained in the second and subsequent steps can be used as an optical resolver. Namely, it is one wherein a layer made of the optically active tris-(2,3-epoxypropyl) isocyanurate or its derivative is formed on the carrier surface in at least one layer, preferably at least two layers, practically from 2 to 20 layers.

A case (the second embodiment) wherein the β-form, α-form or mixed form tris-(2,3-epoxypropyl)isocyanurate is used, will be described. As the carrier, silica gel is used as an example.

In the 1' step, the silica gel surface is treated with e.g. a silane type coupling agent as a compound having a reactive functional group (A), whereby the silica gel surface is chemically modified.

In the 2' step, the reactive functional group (A) in the silane coupling agent chemically bonded on the silica gel surface and tris-(2,3-epoxypropyl)isocyanurate are reacted, so that the carrier surface is chemically modified with the tris-(2,3-epoxypropyl)isocyanurate derivative. (0 Generation)

In the 3' step, a compound (such as ammonia) having a reactive functional group (A) is reacted to the non-reacted epoxy group of the tris-(2,3-epoxypropyl)isocyanurate derivative chemically bonded on this carrier surface.

In the 4' step, tris-(2,3-epoxypropyl)isocyanurate is further reacted to the carrier having the tris-(2,3-epoxypropyl) isocyanurate derivative having active hydrogen (amino group) at its terminal, supported thereon, as obtained in the 3' step, to form two layers of the tris-(2,3-epoxypropyl) isocyanurate derivative, on the silica gel. (The first generation)

The 5' step, et seq. are steps in which the 3' step and the 4' step are repeated to laminate the tris-(2,3-epoxypropyl) isocyanurate layers.

The optical resolver of the present invention is prepared by the following final step. Namely, on the surface of the carrier in the 1' step et seq., a layer of tris-(2,3-epoxypropyl) isocyanurate is formed in at least one layer, preferably at least two layers, practically from 2 to 20 layers, and thereafter, an optically active compound (B) is reacted.

With the carrier having the optically active tris-(2,3-epoxypropyl)isocyanurate or its derivative, or the optically active derivative of tris-(2,3-epoxypropyl)isocyanurate supported thereon, as the optical resolver obtained by the above first or second embodiment, the active points in optical resolution can be increased by the above process, whereby the effective surface area can be increased, and thus it is useful as a packing for high-performance liquid chromatography. Further, in both the first and second embodiments, by using an optically active compound (B) having at least one asymmetric carbon and at least two reactive functional groups (A) in one molecule, instead of e.g. ammonia, the effective points in optical resolution can also be increased, such being further preferred. When the above process is employed, it is further preferred that functional groups which may change with time at the time of using as an optical resolver, should not remain. For example, as such functional groups, non-reacted epoxy groups of the tris-(2,3-epoxypropyl)isocyanurate may be mentioned. This is intended to prevent change with time of the asymmetry-recognizing ability by the reaction with e.g. a solvent such as an alcohol to be used as an eluent in HPLC when such an optical resolver is used.

Accordingly, it is preferred that non-reacted epoxy groups are reacted with e.g. ammonia to convert them into hydroxyl groups and amino groups.

Further, by combining the first embodiment to the second embodiment, i.e. by reacting the optically active compound (B) in the final step of the first embodiment, a synergistic effect by an asymmetric source in the optically active compound and the asymmetric source in tris-(2,3-epoxypropyl)isocyanurate may be obtained, whereby a further preferred optical resolver can be obtained.

EXAMPLES

Now, the present invention will be described in detail with reference to Preparation Examples and Working Examples.

The analytical methods in each Example are shown below.

(1) Organic content-introduction ratio ($T_G$/DTA 220 apparatus for simultaneous thermogravimetry/differential thermal analysis, manufactured by Seiko Instruments Inc.)

From 10 to 19 mg of a sample was weighed and heated to 800° C. at a temperature raising rate of from 30 to 40° C. per minute and maintained at 800° C. for 40 minutes. When the sample reached 200° C., it was deemed to have been completely dried.

Organic content introduction ratio (%)=(W800/W200)×100

W200: weight at the time of 200° C. in the temperature raise.

W800: weight after being held at 800° C. for 40 minutes.

(2) Specific retention volume (k')=((retention time of antipode)−(dead time))/(dead time)

(3) Separation factor ($\alpha$)=k2'/k1' k1': specific retention volume of the first peak k2': specific retention volume of the second peak (4) Optical resolution by high performance liquid chromatography Pump: PU-980 (manufactured by JASCO Corporation)

Degasser: DG-980-50 (manufactured by JASCO Corporation)

Ultraviolet visible light detector: UV-970 (manufactured by JASCO Corporation)

Optical rotation detector: OR-990 (manufactured by JASCO Corporation)

Flow rate: 0.5 ml/min.

Preparation Example 1

Treatment of Silica Gel with Surface Treating Agent 31.19 g of Develosil 100-7 (average particle size: 7 μm, average pore diameter: 120 Å, pore surface area: 350 m²/g) preliminarily dried under reduced pressure at 180° C. for 3 hours, 320 ml of benzene, 5 ml of pyridine and 94 ml of 3-aminopropyl triethoxysilane were put into a flask, and refluxed at a temperature of from 80 to 90° C. for 18 hours with stirring. After cooling to room temperature, the reaction solution was put into 500 ml of methanol, washed and subjected to filtration, followed by washing with methanol and acetone. This was dried to obtain 33.51 g of silica gel having an amino group as an active hydrogen group introduced to the surface. The organic content introduction ratio of the amino group-introduced silica gel thus obtained, was 8%.

Preparation Example 2

Modification of the Silica Gel Surface With tris-(2,3-epoxypropyl)isocyanurate 28.93 g of the amino group-introduced silica gel obtained in Preparation Example 1, 8.21 g of TEPIC-S (high purity product of tris-(2,3-epoxypropyl)isocyanurate, manufactured by Nissan Chemical Industries, Ltd.) and 300 ml of butyl acetate, were reacted at a temperature of from 120 to 140° C. for 21 hours with stirring in a flask. Filtration was carried out, followed by washing with acetone and drying to obtain 33.36 g of tris-(2,3-epoxypropyl)isocyanurate-introduced silica gel. The organic content introduction ratio of the tris-(2,3-epoxypropyl)isocyanurate-introduced silica gel thus obtained, was 22%.

Preparation Example 3

Addition of Ammonia to the tris-(2,3-Epoxypropyl) isocyanurate Introduced to the Silica Gel Surface 32.91 g of the tris-(2,3-epoxypropyl)isocyanurate-introduced silica gel obtained in Preparation Example 2, 15 ml of a 28% ammonia aqueous solution and 200 ml of distilled water were reacted at 40° C. for 24 hours with stirring in a flask. Filtration was carried out, followed by washing with acetone and drying to obtain 32.68 g of terminal amino group tris-(2,3-epoxypropyl)isocyanurate-introduced silica gel. The organic content introduction ratio of the terminal amino group tris-(2,3-epoxypropyl) isocyanurate-introduced silica gel thus obtained, was 22%.

Preparation Example 4

Preparation of an Optical Resolver Having an Optically Active Compound Supported on a Carrier 4.08 g of the terminal amino group tris-(2,3-epoxypropyl) isocyanurate-introduced silica gel obtained in Preparation Example 3 was preliminarily dried in a flask under reduced pressure at a temperature of from 80 to 90° C. for two hours, and into the flask, 80 ml of pyridine and 0.84 g of (S)-(−)-methylbenzyl isocyanate were added and reacted at a temperature of from 80 to 90° C. for 4 hours with stirring. Four hours later, 0.50 g of (S)-(−)-methylbenzyl isocyanate was added, and the reaction was further carried out for 13.5 hours. The solvent was removed by centrifugal separation, followed by washing with acetone and drying to obtain 4.23 g of an optical resolver (1). The organic content introduction ratio of the optical resolver (1) thus obtained, was 27%.

Preparation Example 5

Preparation of Optically Active tris-(2,3-Epoxypropyl)isocyanurate

Into a flask having a capacity of 300 ml and equipped with a stirring apparatus, a thermometer, a continuous dropping apparatus and an apparatus for concentrating an azeotropic vapor of R-epichlorohydrin having an water content of at most 1% and water, under reduced pressure and returning only R-epichlorohydrin to the reaction system, 12.9 g (0.1 mol) of isocyanuric acid, 185 g (2 mol) of R-epichlorohydrin and 0.07 g of tetraethylammonium bromide were added and stirred at 90° C. for 10 hours. Then, the interior of the reaction system was brought to a reduced pressure of 50 mmHg, and while maintaining the internal temperature of the reactor at a level of from 40 to 50° C., 28 g (0.35 mol) of a 50 wt % sodium hydroxide aqueous solution was dropwise added in the entire amount over a period of about 1 hour and reacted. During this period, dropped water and formed water were removed out of the system by azeotropic distillation together with R-epichlorohydrin.

After completion of the reaction, the interior of the reactor was cooled to room temperature, followed by washing by means of a 10% sodium dihydrogen phosphate aqueous solution, thereby to neutralize excessively used sodium hydroxide, and then sodium chloride was removed by washing with water. R-epichlorohydrin was distilled off under reduced pressure (10 mmHg) at 120° C. to obtain 20.5 g of (2R,2'R,2"R)-tris-(2,3-epoxypropyl)isocyanurate. Further, 20.5 g of the obtained (2R,2'R,2"R)-tris-(2,3-epoxypropyl) isocyanurate was put into a 300 ml flask equipped with a stirring apparatus, a thermometer and a reflux condenser, together with 200 ml of methanol and dissolved with stirring at 60° C. Then, it was left to cool naturally at room temperature for recrystallization. The crystals were collected by filtration, washed with methanol and then dried under reduced pressure at 100° C. to obtain 15.2 g of (2R,2'R, 2"R)-tris-(2,3-epoxypropyl)isocyanurate. The (2R,2'R,2"R)-tris-(2,3-epoxypropyl) isocyanurate thus obtained was optically pure. The purity was at least 99%, $[\alpha]_d^{20}=+20.73°$ (c=0.5, $H_2O$). The melting point was from 100.7 to 104.9° C.

Preparation Example 6

Modification of a Silica Gel Surface with Optically Active tris-(2,3-Epoxypropyl)isocyanurate 7.27 g of the amino group-introduced silica gel obtained in Preparation Example 1, 1.51 g of the (2R,2'R,2"R)-tris-(2,3-epoxypropyl)isocyanurate obtained in Preparation Example 5 and 90 ml of butyl acetate were reacted at a temperature of from 80 to 90° C. for 36 hours with stirring in a flask. Filtration was carried out, followed by washing with acetone and drying to obtain 8.29 g of optically active tris-(2,3-epoxypropyl)isocyanurate-introduced silica gel. The organic content introduction ratio of the optically active tris-(2,3-epoxypropyl)isocyanurate-introduced silica gel thus obtained, was 20%. This compound was an optical resolver of the present invention, but in order to make it a better optical resolver, it was decided to continue treatment.

Preparation Example 7

Addition of Ammonia to the Optically Active tris-(2,3-Epoxypropyl)isocyanurate Introduced to the Silica Gel Surface 8.08 g of the optically active tris-(2,3-epoxypropyl)isocyanurate-introduced silica gel obtained in Preparation Example 6, 3.6 ml of a 28% ammonia aqueous solution and 50 ml of distilled water, were reacted at 40° C. for 24 hours with stirring in a flask. Filtration was carried out, followed by washing with distilled water and with acetone, and drying, to obtain 7.84 g of terminal amino group optically active tris-(2,3-epoxypropyl)isocyanurate-introduced silica gel. The organic content introduction ratio of the terminal amino group optically active tris-(2,3-epoxypropyl) isocyanurate-introduced silica gel thus obtained, was 20%. This compound was an optical resolver of the present invention, but in order to make it a better optical resolver, it was decided to continue treatment.

Preparation Example 8

Modification of a Silica Gel Surface with Double Layers of Optically Active tris-(2,3-Epoxypropyl)isocyanurate 7.66 g of the terminal amino group optically active tris-(2,3-epoxypropyl)isocyanurate-introduced silica gel obtained in Preparation Example 7, 1.15 g of the (2R,2'R, 2"R)-tris-(2,3-epoxypropyl)isocyanurate obtained in Preparation Example 5 and 80 ml of butyl acetate were reacted at a temperature of from 80 to 90° C. for 36 hours with stirring in a flask. Filtration was carried out, followed by washing with acetone and drying to obtain 8.44 g of double layer-modified (second generation) optically active tris-(2,3-epoxypropyl)isocyanurate-introduced silica gel. The organic content introduction ratio of the (second generation) optically active tris-(2,3-epoxypropyl)isocyanurate-introduced silica gel thus obtained, was 27%. This compound was an optical resolver of the present invention, but in order to make it a better optical resolver, it was decided to continue treatment.

Preparation Example 9

Addition of Ammonia to the (Second Generation) Optically Active tris-(2,3-Epoxypropyl)isocyanurate Introduced to the Silica Gel Surface (Preparation of an Optical Resolver (2) Having the Optically Active tris-(2,3-Epoxypropyl)isocyanurate Supported on the Carrier)

8.24 g of the (second generation) optically active tris-(2, 3-epoxypropyl)isocyanurate-introduced silica gel obtained in Preparation Example 8, 1.8 ml of a 28% ammonia aqueous solution and 50 ml of distilled water, were reacted at 40° C. for 24 hours with stirring in a flask. Filtration was carried out, followed by washing with distilled water and with acetone, and drying, to obtain 8.21 g of a terminal amino group optically active tris-(2,3-epoxypropyl)isocyanurate-introduced silica gel. The organic content introduction ratio of the terminal amino group optically active tris-(2,3-epoxypropyl)isocyanurate-introduced silica gel (optical resolver (2)) thus obtained, was 26%.

Reference Preparation Example 1

Introduction of an Optically Active Compound Containing no tris-(2,3-Epoxypropyl)isocyanurate Derivative, to the Silica Gel Surface (Preparation of a Comparative Resolver)

3.94 g of the amino group-introduced silica gel obtained in Preparation Example 1was preliminarily dried at a temperature of from 80 to 90° C. for two hours under reduced pressure in a flask, and into the flask, 80 ml of pyridine and 0.52 g of (S)-(–)-methylbenzyl isocyanate were added and reacted at a temperature of from 80 to 90° C. for 4 hours with stirring. Four hours later, 0.25 g of (S)-(–)-methylbenzyl isocyanate was added, and the reaction was further carried out for 14 hours. 14 Hours later, 0.38 g of (S)-(−)-methylbenzyl isocyanate was added, and the reaction was further carried out for 3 hours. The solvent was removed by centrifugal separation, followed by washing with acetone and drying to obtain 3.85 g of a comparative resolver. The organic content introduction ratio of the comparative resolver thus obtained, was 15%.

Example 1

The optical resolver (1) obtained in Preparation Example 4 was packed into a stainless steel column (inner diameter: 4.6 mm, length: 250 mm) by a known slurry packing method, and optical resolution was carried out by using a mixed solution of hexane/ethanol=95/5 (vol/vol) as an eluent.

2,2,2-trifluoro-1-(9-anthryl)ethanol was optically resolved, whereby optical resolution was carried out with $k1'=7.44$ and $\alpha=1.04$, and the (−) isomer eluted first.

Example 2

The optical resolver (2) obtained in Preparation Example 9 was packed into a stainless steel column (inner diameter: 4.6 mm, length: 250 mm) by a known slurry packing method, and optical resolution was carried out by using a mixed solution of hexane/ethanol=95/5 (vol/vol) as an eluent.

Trans-1,2-cyclopropanedicarboxylic acid dianilide was optically resolved, whereby optical resolution was carried out with $k1'=4.13$ and $\alpha=1.07$, and the (−) isomer luted first.

Example 3

The optical resolver (2) obtained in Preparation Example 9 was packed into a stainless steel column (inner diameter: 4.6 mm, length: 250 mm) by a known slurry packing method, and optical resolution was carried out by using a mixed solution of hexane/ethanol=95/5 (vol/vol) as an eluent.

Trans-1,2-cyclobutanedicarboxylic acid dianilide was optically resolved, whereby optical resolution was carried out with $k1'=3.49$ and $\alpha=1.05$, and the (−) isomer eluted first.

Example 4

The optical resolver (2) obtained in Preparation Example 9 was packed into a stainless steel column (inner diameter: 4.6 mm, length: 250 mm) by a known slurry packing method, and optical resolution was carried out by using a mixed solution of hexane/ethanol=95/5 (vol/vol) as an eluent.

Trans-1,2-cyclohexanedicarboxylic acid dianilide was optically resolved, whereby optical resolution was carried out with $k1'=1.67$ and $\alpha=1.04$, and the (+) isomer eluted first.

Example 5

The optical resolver (2) obtained in Preparation Example 9 was packed into a stainless steel column (inner diameter: 4.6 mm, length: 250 mm) by a known slurry packing method, and optical resolution was carried out by using a mixed solution of hexane/ethanol=95/5 (vol/vol) as an eluent.

2,2'-dibenzamide-6,6'-dimethylbiphenyl was optically resolved, whereby optical resolution was carried out with $k1'=6.37$ and $\alpha=1.04$, and the (−) isomer eluted first.

Comparative Example 1

The comparative resolver obtained in Reference Preparation Example 1was packed into a stainless steel column (inner diameter: 4.6 mm, length: 250 mm) by a known slurry packing method, and optical resolution was carried out by using a mixed solution of hexane/ethanol=95/5 (vol/vol) as an eluent.

2,2,2-trifluoro-1-(9-anthryl)ethanol was optically resolved, whereby the optical rotation detector showed no response with $k1'=2.73$ and $\alpha=1.00$, and no optical resolution was carried out.

INDUSTRIAL APPLICABILITY

The present invention provides an optical resolver wherein tris-(2,3-epoxypropyl)isocyanurate itself is an optically active substance, or an optical resolver comprising an optically active derivative of tris-(2,3-epoxypropyl) isocyanurate obtained by reacting an optically active compound to tris-(2,3-epoxypropyl)isocyanurate, or an optical resolver obtained by reacting another optically active compound to optically active tris-(2,3-epoxypropyl) isocyanurate.

Further, the optical resolver is supported on a carrier, whereby it is useful as a packing for high-performance liquid chromatography.

They can be produced by a simple operation. Not only that, it is possible to form a multilayer coating wherein the optically active component is laminated in a plurality of layers on the surface of a carrier, whereby the optical resolving power is high as compared with conventional optical resolvers. Further, by selecting the structure of the optically active component, an environment may be made to be suitable for a compound to be optically resolved, whereby the asymmetry-recognizing ability will be improved, and the optical resolver can be made to be applicable to a wide range of compounds.

What is claimed is:

1. An optical resolver comprising an optically active tris-(epoxyalkyl)isocyanurate or its derivative.

2. The optical resolver according to claim 1, wherein the optically active tris-(epoxyalkyl)isocyanurate is optically active tris-(2,3-epoxypropyl)isocyanurate.

3. An optical resolver comprising an optically active derivative of a tris-(epoxyalkyl)isocyanurate.

4. The optical resolver according to claim 3, wherein the optically active derivative of a tris-(epoxyalkyl)isocyanurate is an optically active derivative of tris-(2,3-epoxypropyl) isocyanurate.

5. The optical resolver according to claim 4, wherein the optically active derivative of tris-(2,3-epoxypropyl) isocyanurate is one obtained by a reaction of tris-(2,3-epoxypropyl)isocyanurate with an optically active compound.

6. An optical resolver having an optically active tris-(epoxyalkyl)isocyanurate or its derivative, or an optically active derivative of a tris-(epoxyalkyl)isocyanurate, supported on a carrier.

7. An optical resolver having optically active tris-(2,3-epoxypropyl)isocyanurate or its derivative, or an optically active derivative of tris-(2,3-epoxypropyl)isocyanurate, supported on a carrier.

8. The optical resolver of claim 1, wherein the alkyl group of the optically active tris-(epoxyalkyl)isocyanurate is an alkyl group having 2–6 carbon atoms.

9. A chromatographic packing comprising the optical resolver of claim 1 and a carrier.

10. The optical resolver of claim 3, wherein the alkyl group of the optically active derivative of tris-(epoxyalkyl) isocyanurate is an alkyl group having 2–6 carbon atoms.

11. The chromatographic packing of claim 9, wherein the carrier is modified with a compound having at least one reactive functional group (A) capable of reacting with an epoxy group and/or an optically active compound (B) having at least one asymmetric carbon and a reactive functional group (A).

12. The optical resolver of claim 1, wherein the optically active tris-(epoxyalkyl)isocyanurate is at least one isocyanurate selected from the group consisting of (2R,2'R,2"R)-tris-(2,3-epoxypropyl)isocyanurate and (2S,2'S,2"S)-tris-(2,3-epoxypropyl)isocyanurate.

13. The optical resolver of claim 2, wherein the optically active tris-(2,3-epoxypropyl)isocyanurate has an optical purity of at least 80% enantiomeric excess.

14. The optical resolver of claim 2, wherein the optically active tris-(2,3-epoxypropyl)isocyanurate has an optical purity of at least 90% enantiomeric excess.

15. The chromatographic packing of claim 11, wherein the carrier is modified with a compound having a reactive functional group (A), and functional group (A) is selected from the group consisting of a carboxylic acid group, an amino group, an imino group, a hydroxyl group, a thiol group, and an isocyanate group.

16. The chromatographic packing of claim 11, wherein the carrier is modified with an optically active compound (B), and compound (B) has an optical purity of at least 90% enantiomeric excess.

17. The chromatographic packing of claim 11, wherein the carrier is modified with an optically active compound (B), and compound (B) has an optical purity of at least 80% enantiomeric excess.

18. The chromatographic packing of claim 9, wherein the carrier is selected from the group consisting of silica, alumina, magnesia, titanium oxide, glass, a silicate, kaolin, polystyrene, polyamide, and polyacrylate.

19. The chromatographic packing of claim 9, wherein the carrier has a particle size of from 1 $\mu$m to 10 mm.

20. The optical resolver of claim 2, wherein the optically active tris-(2,3-epoxypropyl)isocyanurate has a crystalline form selected from the group consisting of $\beta$-form crystal, an $\alpha$-form crystal, and mixtures thereof.

* * * * *